United States Patent
Generoso et al.

(10) Patent No.: US 11,195,618 B2
(45) Date of Patent: Dec. 7, 2021

(54) MULTI-LEVEL MACHINE LEARNING TO DETECT A SOCIAL MEDIA USER'S POSSIBLE HEALTH ISSUE

(71) Applicant: International Business Machines Corporation, Armonk, NY (US)

(72) Inventors: Tiago Dias Generoso, Minas Gerais (BR); Ayron Dal Pont, Hortolandia (BR); Juscelino Candido De Lima Junior, Sao Paulo (BR); Marcos Vinicius L Paraiso, Sao Paulo (BR)

(73) Assignee: International Business Machines Corporation, Armonk, NY (US)

( * ) Notice: Subject to any disclaimer, the term of this patent is extended or adjusted under 35 U.S.C. 154(b) by 419 days.

(21) Appl. No.: 16/033,381

(22) Filed: Jul. 12, 2018

(65) Prior Publication Data

US 2020/0020447 A1 Jan. 16, 2020

(51) Int. Cl.
*G16H 50/20* (2018.01)
*G06Q 50/00* (2012.01)
*G06N 20/00* (2019.01)

(52) U.S. Cl.
CPC ............. *G16H 50/20* (2018.01); *G06N 20/00* (2019.01); *G06Q 50/01* (2013.01)

(58) Field of Classification Search
None
See application file for complete search history.

(56) References Cited

U.S. PATENT DOCUMENTS

| | | | | |
|---|---|---|---|---|
| 9,792,329 B1* | 10/2017 | Cronin | ............... | G06Q 30/0269 |
| 2006/0129427 A1* | 6/2006 | Wennberg | ............. | G06Q 40/08 705/2 |
| 2012/0151047 A1 | 6/2012 | Hodges et al. | | |
| 2013/0279536 A1 | 10/2013 | Choi et al. | | |
| 2013/0325437 A1* | 12/2013 | Lehman | ................... | G06F 40/30 704/9 |
| 2014/0052474 A1* | 2/2014 | Madan | .................... | G16H 50/30 705/3 |
| 2014/0377727 A1 | 12/2014 | Yom-Tov et al. | | |
| 2015/0213225 A1* | 7/2015 | Amarasingham | ....... | G06F 19/00 705/2 |
| 2015/0370994 A1* | 12/2015 | Madan | ................... | G16H 15/00 705/3 |
| 2017/0147775 A1* | 5/2017 | Ohnemus | ............... | G16H 15/00 |
| 2019/0080055 A1* | 3/2019 | Bettencourt Da Silva | ................... | G16H 40/63 |
| 2020/0194123 A1* | 6/2020 | Keohane | ................ | G16H 50/30 |

OTHER PUBLICATIONS

Christina Majaski, "Canada to Use Social Media Data to Detect Mental Illness,." Digital Trends; Mar. 4, 2016.

* cited by examiner

*Primary Examiner* — Jonathan Ng
(74) *Attorney, Agent, or Firm* — Patterson + Sheridan, LLP

(57) ABSTRACT

Techniques for detecting a possible health issue in a user are described. Data related to social media activity for a user is received over a communications network from one or more computing devices. A user analysis profile is generated for the user using a first machine learning model. The user analysis profile includes a personality profile and a mood score. A weighted score associated with potential health issues for the user is determined by classifying the user analysis profile using a second machine learning model. The weighted score exceeds a pre-determined threshold, and electronic notification is provided to a pre-designated person regarding the potential health issue.

14 Claims, 8 Drawing Sheets

MULTI-LEVEL MACHINE LEARNING TO DETECT A SOCIAL MEDIA USER'S POSSIBLE HEALTH ISSUE

BACKGROUND

The present invention relates to machine learning, and more specifically, to using machine learning to detect a possible health issue in a user.

Detecting possible health issues, and particularly a possible mental health issue, for example, depression or anxiety can be challenging. For example, the symptoms of a possible health issue may not be easily identified by people close to the patient, like parents, friends, and teachers. This can be particularly true of adolescents and other young people, for whom possible mental health issues like depression and anxiety can be a major concern. Young people often communicate through communication channels that may be unfamiliar to adults, including internet and social media related communication channels, which can make identification of possible symptoms of health issues even more difficult.

SUMMARY

Embodiments described herein include a method for detecting a possible health issue in a user. The method includes receiving data related to social media activity for a user, over a communications network, from one or more computing devices. The method further includes generating a user analysis profile for the user by analyzing the received data using a first one or more machine learning models, the user analysis profile including a personality profile for the user and a mood score related to a mood of the user. The method further includes determining a weighted score associated with detecting a potential health issue for the user by classifying the user analysis profile using a second one or more machine learning models. The method further includes determining that the weighted score exceeds a pre-determined threshold, and in response providing an electronic notification to a pre-designated person regarding the potential health issue.

Embodiments described herein further include a system. The system includes a processor and a memory storing a program, which, when executed on the processor, performs an operation. The operation includes receiving data related to social media activity for a user, over a communications network, from one or more computing devices. The operation further includes generating a user analysis profile for the user by analyzing the received data using a first one or more machine learning models, the user analysis profile including a personality profile for the user and a mood score related to a mood of the user. The operation further includes determining a weighted score associated with detecting a potential health issue for the user by classifying the user analysis profile using a second one or more machine learning models. The operation further includes determining that the weighted score exceeds a pre-determined threshold, and in response providing an electronic notification to a pre-designated person regarding the potential health issue.

Embodiments herein further include a computer program product for detecting a possible health issue in a user. The computer program product includes a computer-readable storage medium having computer-readable program code embodied therewith, the computer-readable program code executable by one or more computer processors to perform an operation. The operation includes receiving data related to social media activity for a user, over a communications network, from one or more computing devices. The operation further includes generating a user analysis profile for the user by analyzing the received data using a first one or more machine learning models, the user analysis profile including a personality profile for the user and a mood score related to a mood of the user. The operation further includes determining a weighted score associated with detecting a potential health issue for the user by classifying the user analysis profile using a second one or more machine learning models. The operation further includes determining that the weighted score exceeds a pre-determined threshold, and in response providing an electronic notification to a pre-designated person regarding the potential health issue.

DETAILED DESCRIPTION

Figure 1:
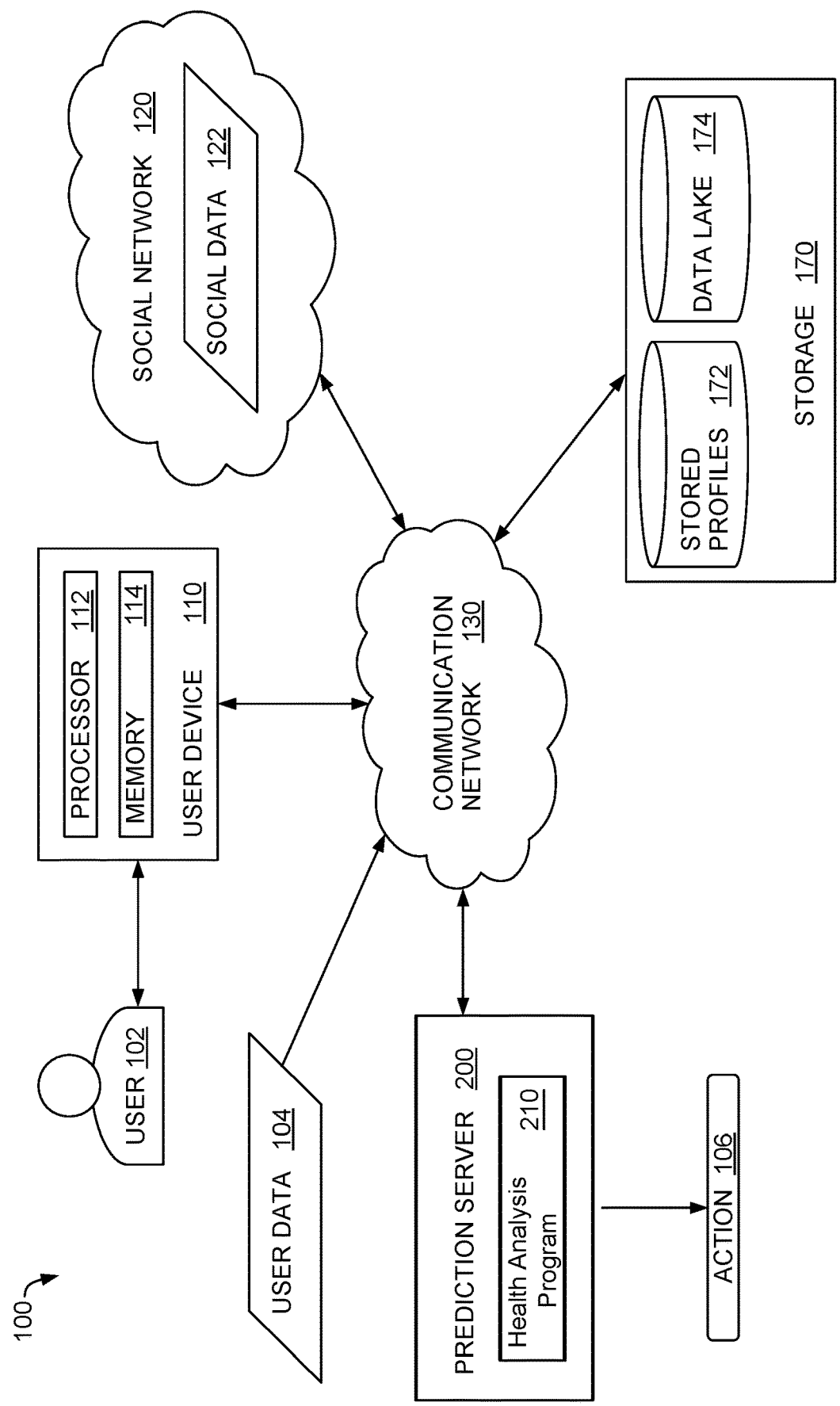
FIG. 1 is a block diagram illustrating a system to detect a possible health issue, using machine learning and social media data, according to an embodiment.

One or more embodiments described herein relate to a solution to provide support for social network users, which can include identifying user behaviors and identifying users with possible health issues. The method and system of the present disclosure can be particularly applicable to teenagers and young people, who are often heavy users of social media, but it is not limited to any specific demographic group. As used herein, a possible health issue can include a possible mental health issue such as depression, anxiety issues, panic issues, and other issues. A possible health issue can also include anger issues, stress, issues related to a user's emotional, psychological, and social well-being, and other potential issues. Before private data is collected or analyzed, a user must consent to the collection and analysis of the private data. Along with data from social medial, data from other sources can be used. For example, Global Positioning System (GPS) data, Internet search content, phone call data, and a variety of other data can be used.

According to one embodiment described herein, four factors are identified based on classifying the collected data using one or more machine learning algorithms. Each of these four factors can then be used in the evaluation. First, a personality profile can be generated for the user. For example, information about a user's social media activity (e.g., frequency of posts, participation in groups, etc.) can be ingested and classified using a trained machine learning model to generate the personality profile. Second, the user's mood can be estimated. As an example, additional information about the user's social media activity (e.g., the content of the user's posts, frequency of likes on friends' posts, etc.) can be ingested and classified using a trained machine learning model to generate a mood score reflecting the user's current mood. Third, any bullying of the user by others can be detected. For example, social media data can be used to detect this as well—information about the user's social media activity (e.g., comments by others on the user's posts, the number of comments on the user's posts removed by the social media administrators, etc.) can be ingested and classified using a trained machine learning model to identify instance of bullying. And finally, psychological symptoms can be identified (e.g., again using social media information, like information about events occurring in the user's life).

These factors can be correlated, and additional machine learning tools can be used to classify the data and detect a possible health issue in the user. If an issue is identified, remedial actions can be taken. For example, a pre-defined contact person like a family member, friend, or other responsible party can be identified and notified. As another example, social media posts designed to alleviate the symptoms of the issue can be generated and provided to the user. Further, therapeutic or motivational messages can be provided to the user. As another example, potentially problematic social media posts or comments can be blocked or removed.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

FIG. 1 is a block diagram illustrating a system to detect a possible health issue, using machine learning and social media data, according to an embodiment. A user 102 has one or more user devices 110 that include a processor 112 and a memory 114. The user devices 110 can be any suitable user device, including a smartphone, tablet, laptop computer, desktop computer, or other suitable device. The processor 112 may be any computer processor capable of performing the functions described herein. Further, the processor 112 may be a single processor, multiple processors, a processor with a single core, a processor with multiple cores, or any other suitable configuration. Although memory 114 is shown as a single entity, the memory 114 may include one or more memory devices having blocks of memory associated with physical addresses, such as random access memory (RAM), read only memory (ROM), flash memory or other types of volatile and/or non-volatile memory.

The user device 110 is in communication with the communication network 130. The communication network 130 can be any suitable communication network, including a cellular network, the Internet, a local access network, a mesh network, or a wide access network. The communication network 130 can use any suitable communication protocol, including any suitable wireless or wired protocol. The user device 110 can communicate with the social network 120 via the communication network 130.

The social network 120 is also in communication with the communication network 130. The social network 120 can be any suitable social network, including an Internet-based social network that facilitates communication between users over the internet. The social network 120 includes the social data 122. In an embodiment, the social data 122 includes data related to use of the social network 120 by the user 102. For example, the social data 122 can include data related to posts on the social network 120 made by the user 102, favorites on the social network 120 by the user 102, likes on the social network 120 by the user 102, views of content on the social network 120 by the user 102, and any other relevant information.

The prediction server 200 is also in communication with the communication network 130. The prediction server 200 is discussed in more detail with regard to FIG. 2. The prediction server 200 includes a health analysis program 210. The health analysis program 210 is generally configured to detect a social media user's possible health issue and propose an action 106. In an embodiment, the health analysis program 210 can include the analytics engine 220, the prediction module 230, and the action module 240. Alternatively, the health analysis program 210 can include other suitable modules for detecting a social media user's possible health issue. As illustrated in FIG. 1, the health analysis program 210 is stored on the prediction server 200. The health analysis program 210 can be stored locally in the prediction server 200, or can be stored remotely so that it is accessible via the communication network 130 (e.g., stored in the storage 170). Alternatively, as discussed in more detail with regard to FIGS. 7 and 8, the health analysis program 210 can be implemented using a cloud solution.

The prediction server 200 can access additional user data 104 via the communication network 130. The user data 104 includes additional data related to the user 102, in addition to the social data 122. For example, and as discussed further below, the user data 104 can include key-logger data, GPS positional data, phone logger data, and many other types of data. The prediction server 200 also has access to the social data 122 via the communication network 130. In an embodiment, the prediction server 200 can determine one or more actions 106.

The storage 170 is further in communication with the communication network 130. The storage 170 includes the stored profiles 172. In an embodiment, and as discussed further below, the prediction server 200 can generate one or more profiles for the user 102. These profiles can be stored in the storage 170 as stored profiles 172. The stored profiles 172 can be stored in a database, including a relational or a non-relational database, or in any other suitable storage device.

The storage 170 further includes the data lake 174. In an embodiment, the data lake 174 can be a relatively large data container for storing data for use by the prediction server 200. As discussed wither regard to FIG. 2, the prediction server 200 can include various cognitive and machine learning modules. The data lake 174 can be used to store data and information for use by these modules.

Figure 2:
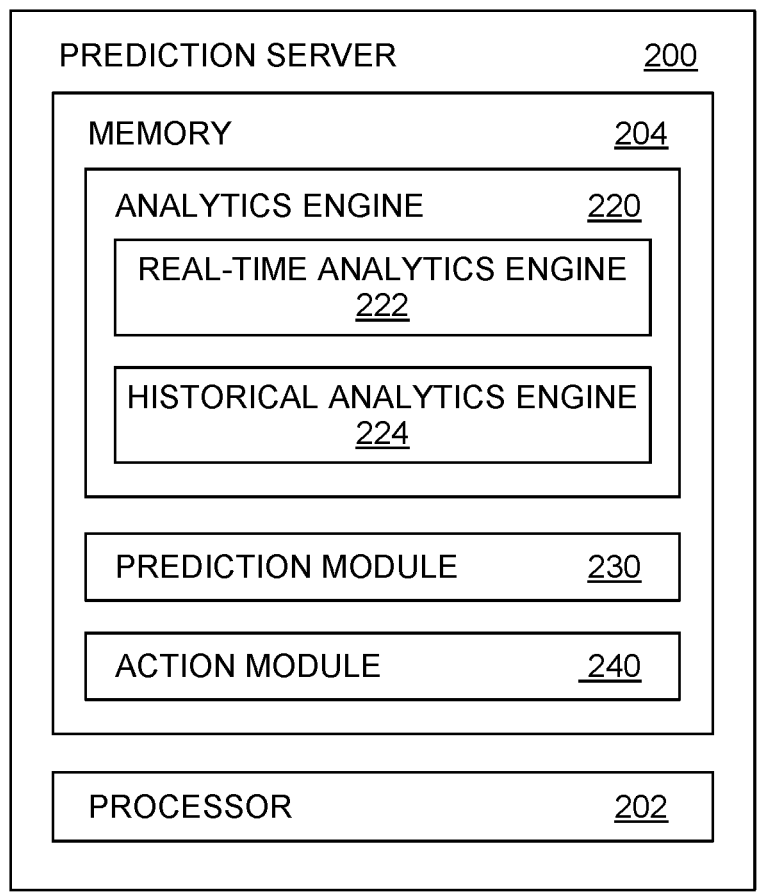
FIG. 2 is a block diagram illustrating a prediction server for use in detecting a possible health issue, using machine learning and social media data, according to an embodiment.

FIG. 2 is a block diagram illustrating the prediction server 200. In the illustrated embodiment of FIG. 2, the prediction server 200 is depicted as a single server. But in other implementations, the prediction server 200 can be made up of many different connected computers (e.g., connected over a communication network or via a direct connection). Further, as discussed above, the prediction server 200 can be provided to end users through a cloud computing infrastructure. The prediction server 200 includes a processor 202. The processor 202 generally retrieves and executes programming instructions stored in the memory 204. The processor 202 is included to be representative of a single central processing unit (CPU), multiple CPUs, a single CPU having multiple processing cores, graphics processing units (GPUs) having multiple execution paths, and the like. The memory 204 is generally included to be representative of electronic storage of any suitable type(s), including random access memory or non-volatile storage.

The memory 204 generally includes program code for performing various functions related to detecting a possible health issue, using machine learning and social media data. The program code is generally described as various functional "applications," "components," or "modules" within the memory 204, although alternate implementations may have different functions and/or combinations of functions. Within the memory 204, the analytics engine 220 is generally configured to analyze the user data 104 and the social data 122 to prepare the data for use by the prediction module 230 and the action module 240. This is discussed in more detail with regard to FIG. 3.

The analytics engine 220 includes a real-time analytics engine 222 used to ingest real-time data for the user 102. The analytics engine 220 further includes a historical analytics engine 224 to ingest historical data for the user 102. For example, the historical analytics engine 224 can ingest the social data 122 or other relevant historical data. In an embodiment, the historical analytics engine 224 can ingest data stored in the data lake 174 and can store the processed data back in the data lake 174. Both the real-time analytics engine 222 and the historical analytics engine 224 are discussed in more detail with regard to FIG. 3.

The memory 204 further includes the prediction module 230 and the action module 240, according to the illustrated embodiment. The prediction module 230 is generally configured to use machine learning to identify potential anomalies in the user's health, including the user's mental health, based on the data ingested by the analytics engine 220. The action module 240 is generally configured to use further machine learning to analyze the results of the prediction module 230 and determine an appropriate remedial action (e.g., an action 106 illustrated in FIG. 1). Each of these modules is discussed in more detail with regard to FIG. 3.

Figure 3:
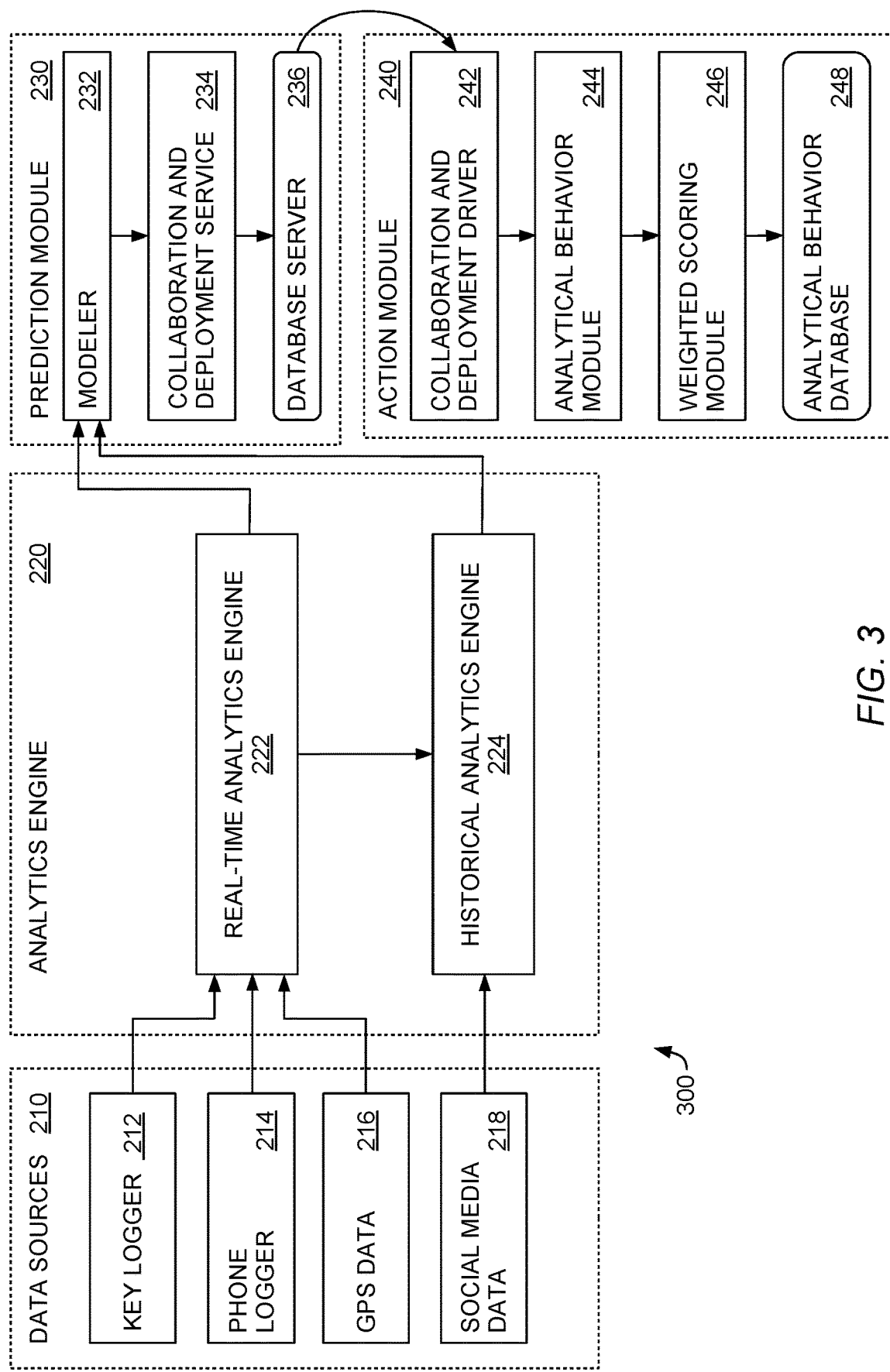
FIG. 3 is a block diagram illustrating data flow in a system to detect a possible health issue using machine learning and social media data, according to an embodiment.

FIG. 3 is a block diagram illustrating data flow in a system 300 to detect a possible health issue using machine learning and social media data, according to an embodiment. In an embodiment, the system 300 can be implemented using the prediction server 200 illustrated in FIG. 2. The system 300 includes the data sources 210. The data sources 210 can include real-time data sources for a user 102 (or several users) and historical data sources for the user 102 (or the several users). For example, as illustrated in FIG. 3, the data sources 210 can include a key logger 212, a phone logger 214, and GPS data 216.

In an embodiment, a user device (e.g., the user device 110 illustrated in FIG. 1) can include a user-safety monitoring component resident in the memory 114, enabled with the permission of an administrator for the user device. This administrator could be, for example, a parent or guardian concerned about the safety of a child using the device. Alternatively, the administrator could be the user him or herself. The user safety monitoring component can include applications resident on the memory 114 of the user device 110, like a key logger 212 used to log and transmit a record of keystrokes by the user on the user device 110, a phone logger 214 used to log and transmit a record of voice calls by the user on the user device 110, and a GPS module to track the location of the user device 110 and provide the GPS data 216. These are examples of real-time data. The data sources 210 can include any other suitable data sources, including biometric data relating to a user, images of or relating to the user, additional voice or sound relating to the user, etc.

The data sources 210 can also include the social media data 218 (e.g., the social data 122 illustrated in FIG. 1). In an embodiment, the social media data 218 is an example of historical data because it relates to the user 102's historical usage of social media platforms (e.g., the social network 120). The data sources 210 illustrated in FIG. 3 are merely examples of suitable data sources—other data sources can be used, instead of or in addition to the illustrated data sources 210.

The system 300 further includes the analytics engine 220. In the embodiment illustrated in FIG. 3, data from the real-time data sources (e.g., key logger 212, phone logger 214, and GPS data 216) is provided to the real-time analytics engine 222. This data can be provided directly to the real-time analytics engine 222, or it can be stored in a suitable electronic database and retrieved by the real-time analytics engine 222 from the database. For example, the real-time data could be stored in the data lake 174 and retrieved by the real-time analytics engine 222 from the data lake 174 using a suitable request or query. In an embodiment, the real-time analytics engine 222 can be implemented using the IBM® InfoSphere® Streams software platform. Alternatively, the real-time analytics engine 222 can be implemented using another suitable software platform.

The real-time analytics engine 222 ingests the input data and pre-processes it for use by the machine learning components of the prediction module 230 and the action module 240. For example, the real-time analytics engine 222 can analyze raw information from the key logger 212, the phone logger 214, and the GPS data 216 and optimize it by removing unnecessary or extraneous information. The real-time analytics engine 222 can also perform speech-to-text and image recognition functionality. For example, in order to facilitate the use of audio or video input to the prediction module 230 and the action module 240.

Further, the real-time analytics engine 222 can process the data to put it in a more suitable form for use by the prediction module 230 and the action module 240. For example, the real-time analytics engine can generate feature vectors related to the input data. In this embodiment, a feature vector is a vector having any number of dimensions which represents a numerical representation of the associated electronic data. In some embodiments, this vectorization of electronic data may improve the speed, efficiency, and/or accuracy of the system. In some embodiments, the vectorization of the electronic data is required for the prediction module 230 and the action module 240 to process the input.

In an embodiment, after ingesting the real-time input data (e.g., from the key logger 212, the phone logger 214, and the GPS data 216), the real-time analytics engine can store the processed data in a suitable electronic database, like the data lake 174. The historical analytics engine 224 can retrieve the processed data from the data lake 174. Alternatively, the real-time analytics engine 222 can provide the processed data directly to the historical analytics engine 224.

The historical analytics engine 224 ingests the social media data 218 (and any other suitable data, including output from the real-time analytics engine 222) and preprocesses it for use by the machine learning components of the prediction module 230 and the action module 240. For example, the historical analytics engine 224 can analyze a user's social media posts, likes, favorites, etc. and process this data for use by the prediction module 230 and the action module 240. Like the real-time analytics engine 222 the historical analytics engine 224 can optimize the data by removing unnecessary or extraneous information. The historical analytics engine 224 can also perform speech-to-text and image recognition functionality. For example, in order to facilitate the use of audio or video input to the prediction module 230 and the action module 240.

Further, like the real-time analytics engine 222, the historical analytics engine 224 can generate feature vectors related to the input data. In an embodiment, the historical analytics engine 224 can be implemented using the IBM® InfoSphere® BigInsights™ software platform. Alternatively, the historical analytics engine 224 can be implemented using another suitable software platform. In an embodiment, the real-time analytics engine 222 and the historical analytics engine 224 store the processed data in a suitable electronic database (e.g., the data lake 174), and the prediction module 230 retrieves the data. Alternatively, the real-time analytics engine 222 and the historical analytics engine 224 provide the data directly to the prediction module 230.

The system 300 further includes the prediction module 230. The prediction module 230 is generally configured to identify potential anomalies related to the user's health, including the user's mental health, using machine learning and data from the analytics engine 220. According to the illustrated embodiment, the prediction module 230 includes a modeler 232, a collaboration and deployment service 234 and a database server 236. The modeler 232 is generally configured to generate and maintain one or more machine learning models. In an embodiment, the machine learning models are supervised models initially generated through a training process. Training is discussed in more detail with regard to FIG. 6. The modeler 232 both generates the machine learning models during training, and refines the models based on input data from the analytics engine 220.

The collaboration and deployment service 234 analyzes the data output from the analytical engine 220 using the one or more machine learning models generated by the modeler 232. As discussed in more detail with regard to FIGS. 4 and 5, the collaboration and deployment service 234 can identify potential anomalies related to a user's health, based on the data output by the analytical engine. For example, as illustrated in FIG. 5, the collaboration and deployment service 234 can generate a user analysis profile for the user that includes a personality profile for the user (e.g., the user 102), a mood score relating to the user's current mood, information about instances of bullying of the user, and information about psychological symptoms exhibited by the user. This can be based on processing the real-time and historical data from the data sources 210, using the machine learning models generated by the modeler 232. In an embodiment, the modeler 232 and collaboration and deployment service 234 can be implemented using the IBM® SPSS® Modeler and IBM® SPSS® Collaboration and Deployment Services software platforms. In other embodiment, other suitable software platforms can be used. The collaboration and deployment service 234 can store the output from the machine learning models in a database server 236 (e.g., the data lake 174).

The system 300 further includes the action module 240. The action module 240 is generally configured to determine a weighted score related to detecting a possible health issue, using output from the prediction module 230 and further machine learning techniques. In the illustrated embodiment, the action module 240 includes the collaboration and deployment driver 242, the analytical behavior module 244, the weighted scoring module 246, and the analytical behavior database 248.

The collaboration and deployment driver 242 and the analytical behavior module 244 are generally configured to take the identified potential anomalies from the prediction module 230 and identify a potential health issue in the user. For example, as discussed above (and in more detail with regard to FIG. 5), the prediction module 230 can generate a user analysis profile for the user that includes a personality profile for the user (e.g., the user 102), a mood score relating to the user's current mood, information about instances of bullying of the user, and information about psychological symptoms exhibited by the user. The collaboration and deployment driver 242 and the analytical behavior module 244 can analyze these inputs, together, to identify a potential health issue in the user. This can be done using additional machine learning techniques. In an embodiment, the collaboration and deployment driver 242 and the analytical behavior module 244 can use the machine learning models generated by the modeler 232. Alternatively, the collaboration and deployment driver 242 and the analytical behavior module 244 can use a different machine learning model.

The weighted scoring module 246 takes the output from the collaboration and deployment driver 242 and the analytical behavior module 244 and determines weights for the potential health issue (s). In an embodiment, the weighted scoring module 246 can further consider historical data relating to the user's previous behavior and diagnoses, and previous determinations by the prediction module 230 and the action module 240. In this way, the action module 240 can include a continuous learning mechanism to learn from previous evaluations of the user. Further, the prediction module 230 and the action module 240 can take as input previous evaluations of other users. The output from the weighted scoring module 246 is stored in an analytical behavior database 248 (e.g., the data lake 174), where it can be used to determine a potential remedial action for the user.

Figure 4:
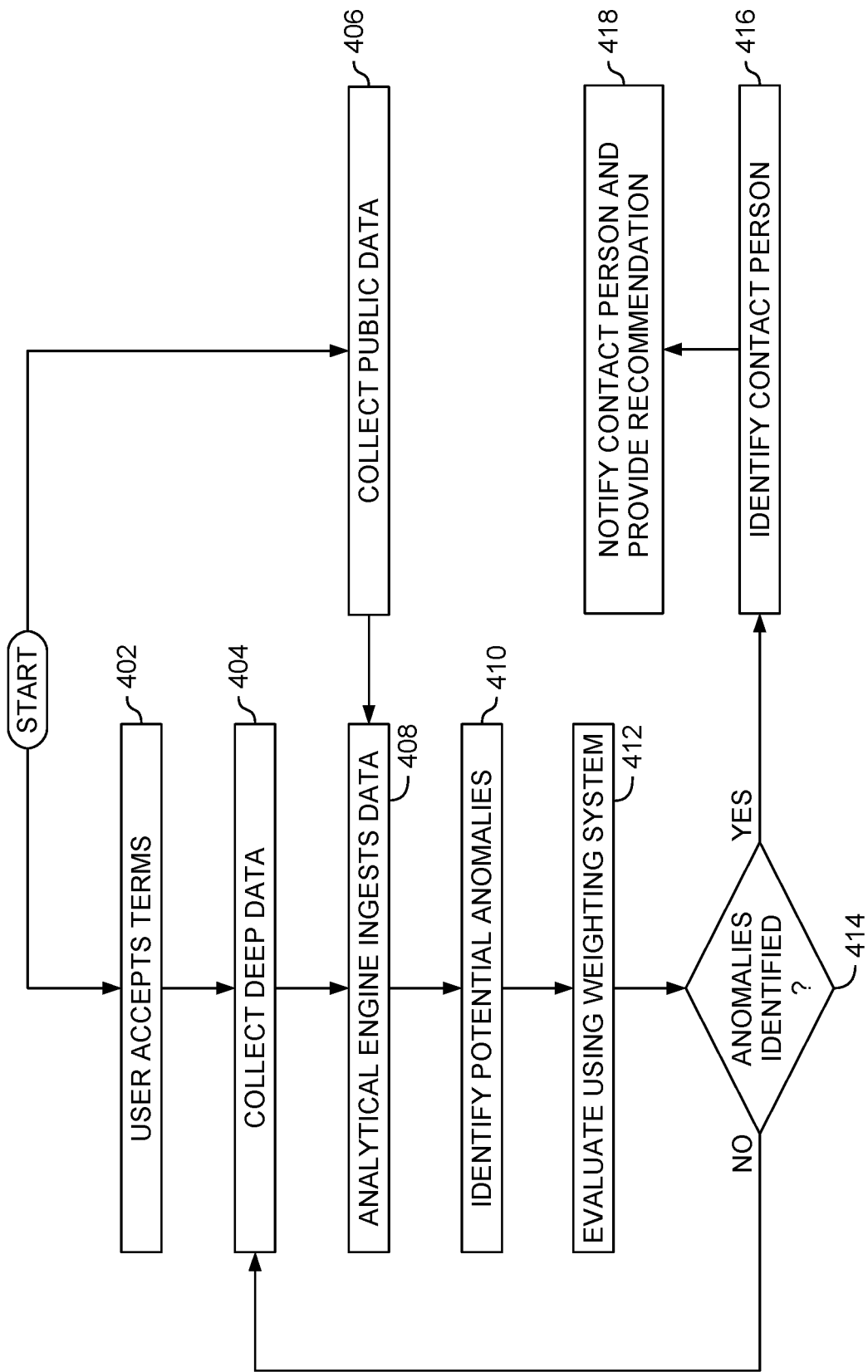
FIG. 4 is a flow chart illustrating detecting a possible health issue using machine learning and social media data, according to an embodiment.
Figure 5:
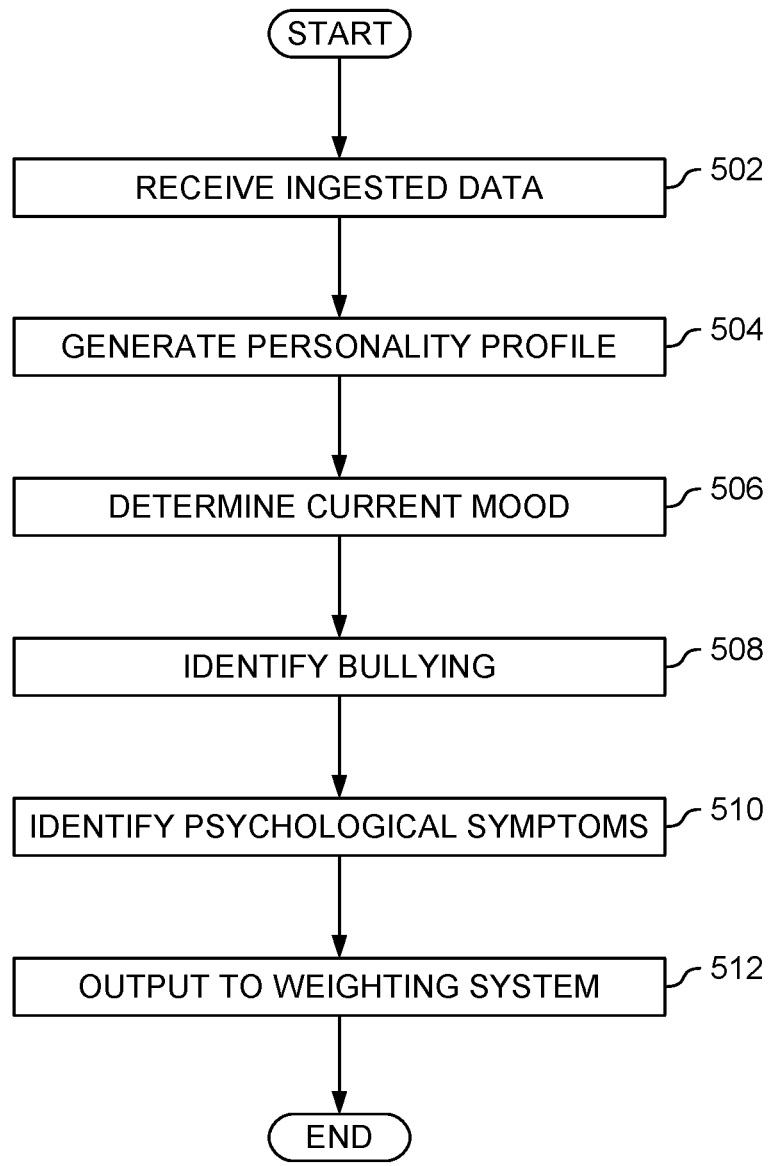
FIG. 5 is a flow chart illustrating identifying potential anomalies related to detecting a possible health issue using machine learning and social media data, according to an embodiment.

FIG. 4 is a flow chart illustrating detecting a possible health issue using machine learning and social media data, according to an embodiment. At block 402, the user accepts terms allowing his or her data to be collected and analyzed. In an embodiment, if the user is a minor the user's parent or guardian could also be required to accept terms for data collection and analysis. If the user does not accept the terms in block 402, the flow ends. At block 404, deep data for the user is collected. As illustrated in FIG. 3, this includes data from the data sources 210, and includes the social media data 218. This data is provided to the analytical engine. At block 408, the analytical engine (e.g., the analytical engine 220 illustrated in FIG. 3), ingests the data. In the illustrated embodiment, at block 406 public data related to the user is collected and also provided to the analytical engine. At block 408, the analytical engine ingests this public data as well.

At block 410, potential anomalies relating to the user's health are identified. This can be done, for example, by the prediction module 230 illustrated in FIG. 3. Block 410 is discussed in more detail with regard to FIG. 5. At block 412, the potential anomalies are evaluated using a weighting system. In an embodiment, this can be done using the action module 240 illustrated in FIG. 3. Alternatively, this can be done using a combination of the prediction module 230 and the action module 240 illustrated in FIG. 3.

At block 414, the system (e.g., the action module 240) determines whether possible health anomalies with a sufficient weight to raise a concern have been identified. This can be done, for example, by comparing the classified weight with a pre-determined threshold. If not, the flow returns to block 404. If so, the system recommends one or more actions. For example, in the illustrated embodiment, at block 416 a contact person is identified. This contact person could be a parent or guardian for the user, a friend, a sibling, or any other suitable person. At block 418, the contact person is notified about the potential health concern. In an embodiment, a recommendation as to the nature of the possible health concern and potential further remedial actions can be provided.

Instead of, or in addition to, notifying a contact person, at block 416 different remedial actions can be taken. These actions can be identified using the action module 240. As one example, the social network 120 could be notified to help the user avoid problematic people or content on the social network. The social network 120 could then modify the user's experience to help avoid problematic content. In another example, the user could be provided with a therapeutic message. In another example, the system could be configured to block information (e.g., social media posts or content) identified as potentially problematic.

FIG. 5 is a flow chart illustrating identifying potential anomalies (which is introduced and identified at block 410 in FIG. 4) related to detecting a possible health issue using machine learning and social media data, according to an embodiment. In an embodiment, the flow chart of FIG. 5 corresponds to block 410 in FIG. 4 and is implemented by the prediction module 230. At block 502, the prediction module 230 receives ingested data from the analytics engine 220. As discussed above with regard to FIG. 3, in an embodiment this data can be provided directly from the analytics engine 220 to the prediction module 230. In another embodiment the analytics engine 220 can store the data in a database (e.g., the data lake 174), and the prediction module 230 can retrieve the data from the database.

At block 504, the prediction module 230 generates the first element in a user analysis profile for the user (e.g., the user 102): a personality profile for the user. In an embodiment, this personality profile can be based at least partially on analysis of the social media data 218. For example, user activity on a social network (e.g., the social network 120) can be used. This can include data about post frequency, participation in groups, interaction with friends and comments on friends' posts, etc. The personality profile can be based on the user's history of activity (e.g., noting a change in activity level), and on users with similar demographics (e.g., similar age, living in a similar area, attending a similar school, etc.). In an embodiment, a so-called "Big Five" personality test can be used to generate the personality profile. In an embodiment, the personality profile can be stored in the stored profiles 172, illustrated in FIG. 1. Further, previously stored profiles can be retrieved from the stored profiles 172 and used in determining the user's personality profile.

At block 506, the prediction module 230 generates the second element in a user analysis profile: a mood score relating to the user's current mood. In an embodiment, the mood identification can also be based at least partially on analysis of the social media data 218. For example, a user's comments could be analyzed to identify recent laughter or positive comments, or negative comments. Further, image and voice recognition can be used. For example, a picture of the user could be analyzed to determine the user's facial expression and the sentiment expressed by the facial expression. As another example, the tone of the user's voice in conversations could be analyzed to determine a positive (or negative) tone or inflection. Further, the content of the user's conversations (spoken or written) could be analyzed.

At block 508, the prediction module 230 generates the third element in a user analysis profile for the user by identifying any bullying of the user. Again, this can also be based at least partially on analysis of the social media data 218. For example, the comments on a user's social media posts could be analyzed. As another example, the number of comments removed from the posts could be analyzed. Further, patterns related to the comment can be identified (e.g., comments on a user's physical appearance, religious or political preferences, etc.). In addition, any other interaction between the user and other people could be analyzed.

At block 510, the prediction module 230 generates the fourth element in a user analysis profile for the user by identifying symptoms of psychological issues (e.g., depression or anxiety issues). The prediction module 230 can consider data about external events in the user's life (e.g., the death of a loved one), a reduction in social activity (e.g., a reduction in social network activity, or a reduction in real-life interactions with others), GPS data (e.g., showing a reduction in movement), internet search activity, and other suitable data. At block 512, the output from blocks 504, 506, 508, and 510 is output to the weighting system. For example, this information can be output to the action module 240. In an embodiment, the action module 240 can consider each of these four factors in evaluating whether the user is exhibiting a possible health issue.

Numerous criteria related to the possible health issue can be used to identify a potential health issue. The embodiment illustrated in FIG. 5 merely provides examples of suitable criteria. For example, information related to potential anger issues in the user (e.g., content posted to social media or other places expressing anger) can be identified and included in the user analysis profile for the user. Further, other forms of aggressive or potentially problematic behavior in others (in addition to bullying), can be identified and included in the user analysis profile.

Figure 6:
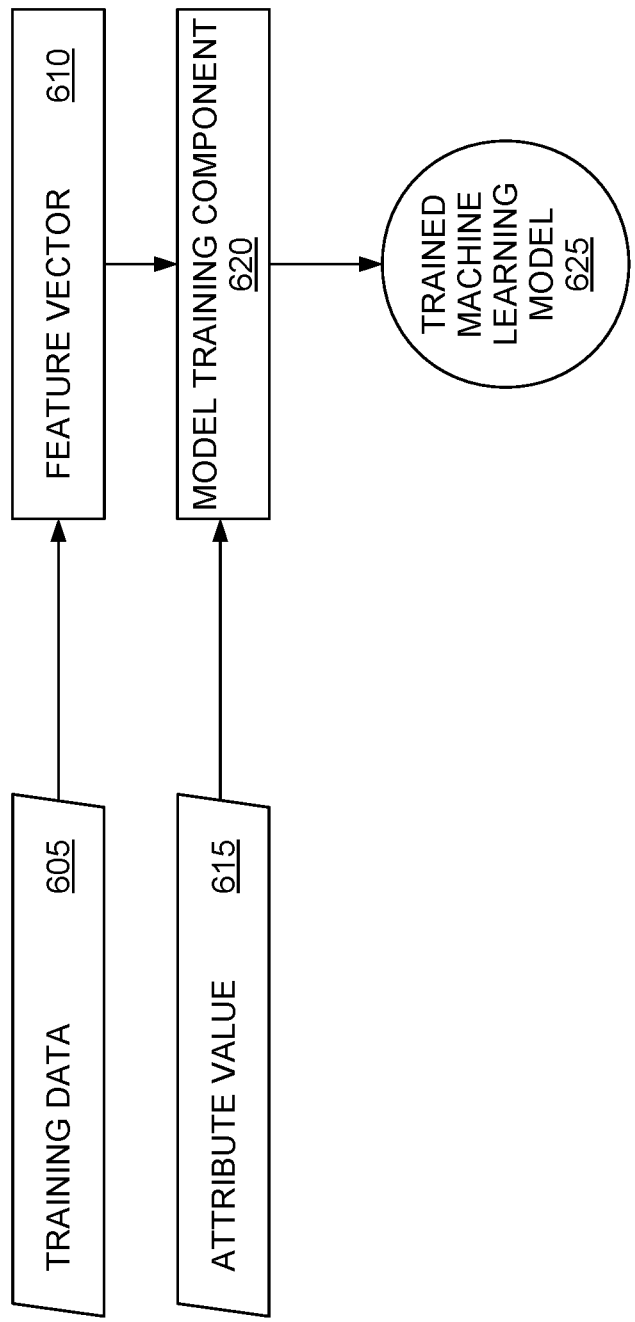
FIG. 6 is a block diagram illustrating training of a machine learning model, according to an embodiment.

FIG. 6 illustrates generating and updating a supervised machine learning model, according to an embodiment. As used herein, "trained machine learning" is used interchangeably with "supervised machine learning," and generally refers to machine learning that utilizes exemplars and pre-determined attribute scores to train the model. As illustrated, a corpus of training data 605 is converted into feature vectors 610. These feature vectors 610 are provided to a model training component 620 (e.g., the modeler 232 illustrated in FIG. 3), along with a set of associated attribute values 615. That is, the training data 605 is associated with one or more attribute values 615 for the principle attributes used by the system, wherein each of the one or more attribute values 615 represents a measure of an attribute indicated by the corresponding training data 605. For example, a negative comment from a friend on a social media post could indicate a higher bullying score, while laughter from a user could indicate a higher mood score. The model training component 620 uses supervised machine learning techniques to generate and update a trained machine learning model 625, which can then be used to process new electronic data. Such techniques may include classification and regression techniques, among others. In this way, an updated model can be maintained.

Figure 7:
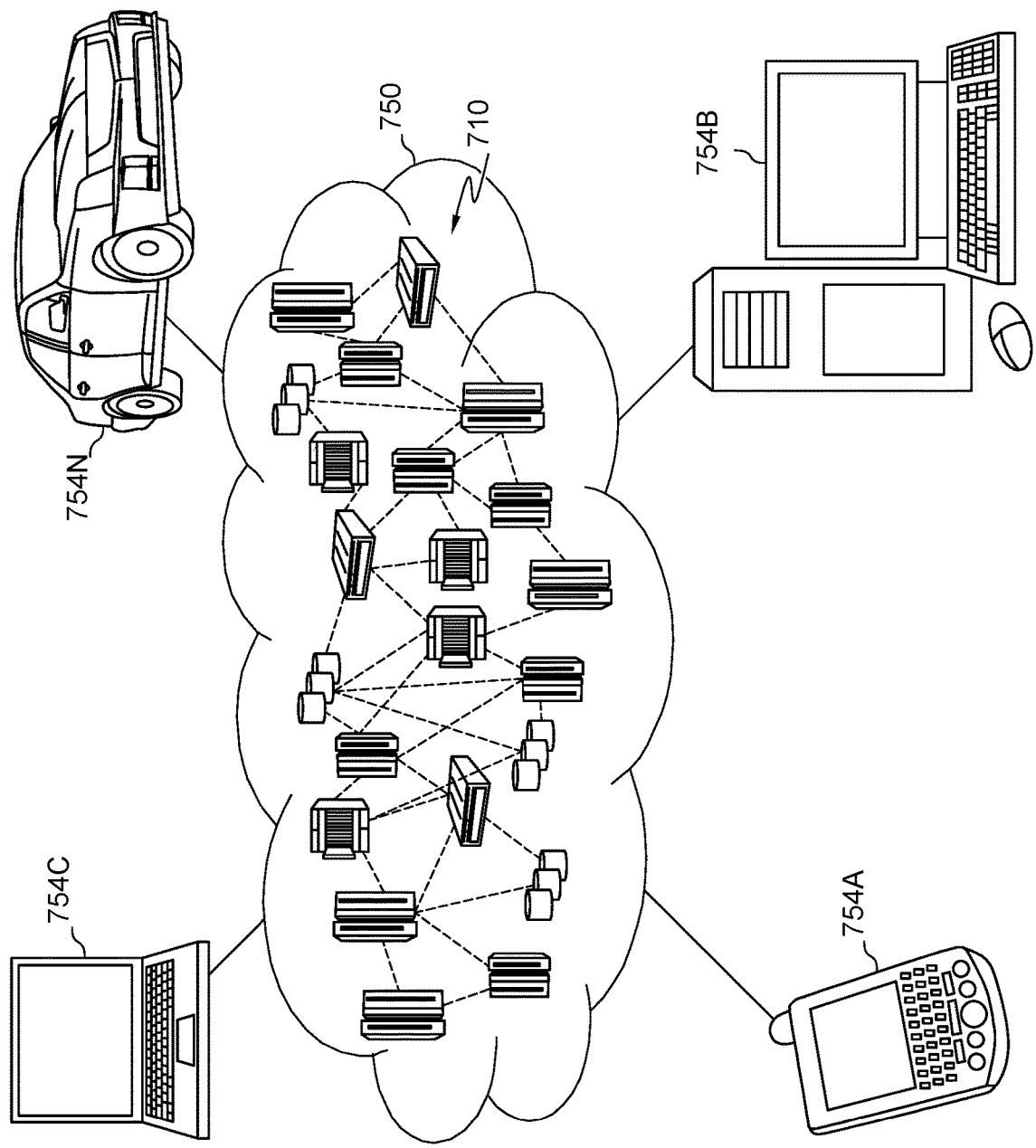
FIG. 7 depicts a cloud computing environment, according to an embodiment.

FIG. 7 depicts a cloud computing environment, according to an embodiment. It is to be understood that although this disclosure includes a detailed description on cloud computing, implementation of the teachings recited herein are not limited to a cloud computing environment. Rather, embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 7, illustrative cloud computing environment 750 is depicted. As shown, cloud computing environment 750 includes one or more cloud computing nodes 710 with which local computing devices used by cloud consumers, such as, for example, personal digital assistant (PDA) or cellular telephone 754A, desktop computer 754B, laptop computer 754C, and/or automobile computer system 754N may communicate. Nodes 710 may communicate with one another. They may be grouped (not shown) physically or virtually, in one or more networks, such as Private, Community, Public, or Hybrid clouds as described hereinabove, or a combination thereof. This allows cloud computing environment 750 to offer infrastructure, platforms and/or software as services for which a cloud consumer does not need to maintain resources on a local computing device. It is understood that the types of computing devices 754A-N shown in FIG. 7 are intended to be illustrative only and that computing nodes 710 and cloud computing environment 750 can communicate with any type of computerized device over any type of network and/or network addressable connection (e.g., using a web browser).

Figure 8:
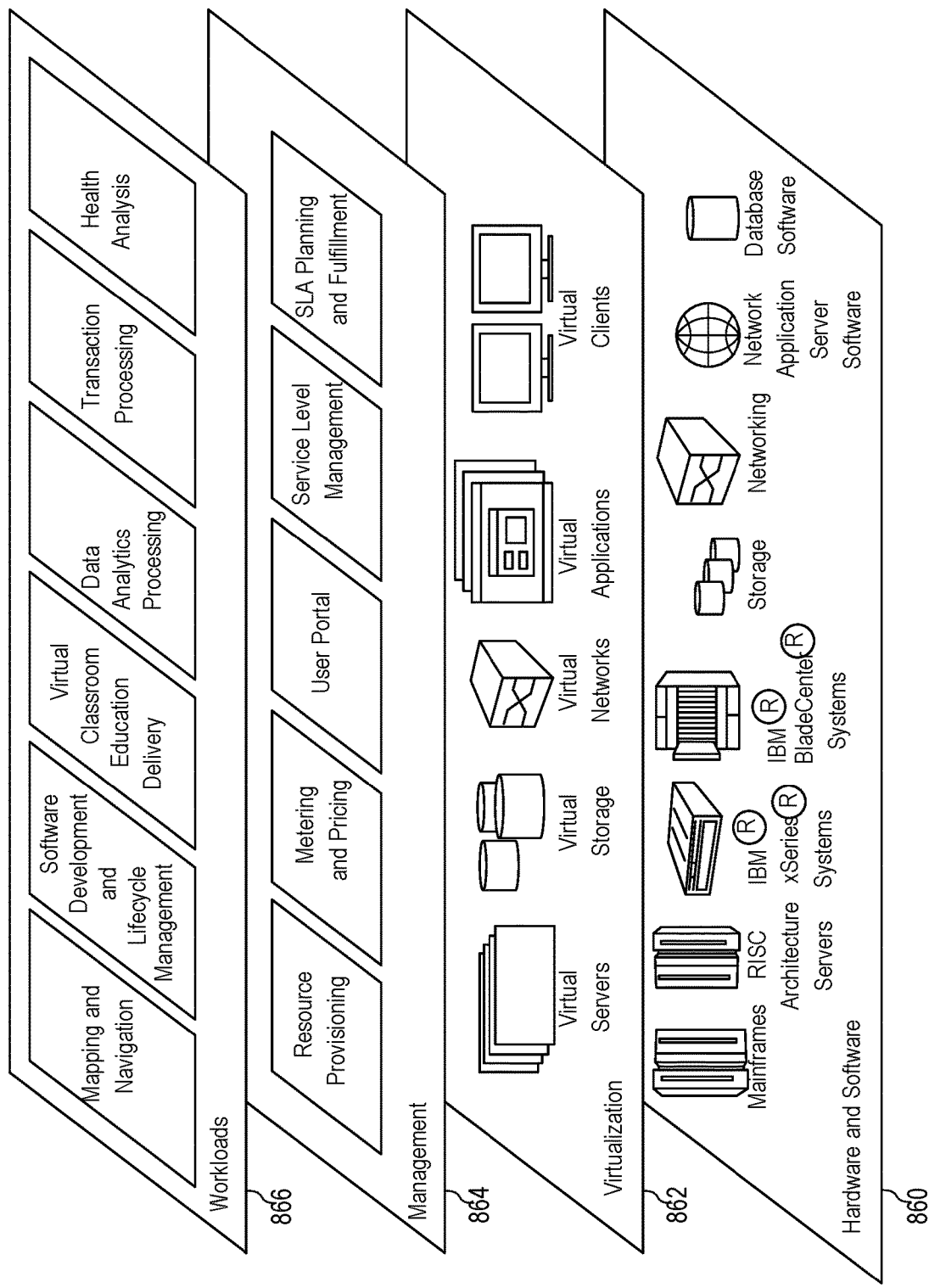
FIG. 8 depicts abstraction model layers, according to an embodiment.

Referring now to FIG. 8, a set of functional abstraction layers provided by cloud computing environment 750 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 860 includes hardware and software components. Examples of hardware components include: mainframes; RISC (Reduced Instruction Set Computer) architecture based servers; servers; blade servers; storage devices; and networks and networking components. In some embodiments, software components include network application server software and database software.

Virtualization layer 862 provides an abstraction layer from which the following examples of virtual entities may be provided: virtual servers; virtual storage; virtual networks, including virtual private networks; virtual applications and operating systems; and virtual clients.

In one example, management layer 864 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 866 provides examples of functionality for which the cloud computing environment may be utilized. Examples of workloads and functions which may be provided from this layer include: mapping and navigation; software development and lifecycle management; virtual classroom education delivery; data analytics processing; transaction processing; and health analysis. In an embodiment, some or all of the modules of the prediction server 200 could be implemented in the workloads layer 866. For example, the health analysis program 210 could be implemented in the workloads layer 866. In an embodiment, the analytics engine 220 could execute on a computing system in the cloud (e.g., in the workloads layer 866) and ingest data from the data sources 210 (e.g., data stored in the hardware and software layer 860). The source data and ingested data could be stored in the cloud. In such a case, the prediction module 230 and the action module 240 could analyze the ingested data and store related data at a storage location in the cloud. Doing so allows access to this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method for detecting a possible health issue in a user, the method comprising:
   receiving data related to social media activity for a user, over a communications network, from one or more computing devices at a computing system comprising:
      a first machine learning model trained to generate user analysis profiles using social media activity, wherein the first machine learning model is trained using a first plurality of feature vectors generated from training data comprising a first plurality of pre-determined attribute values relating to generating the user analysis profiles using social media activity; and
      a second machine learning model trained to generate weighted scores associated with detecting potential health issues using the user analysis profiles output from the first machine learning model, wherein the first machine learning model is different than the second machine learning model, and wherein the first machine learning model is trained using different training data than the second machine learning model, and wherein the second machine learning model is trained using a second plurality of feature vectors generated from training data comprising a second plurality of pre-determined attribute values relating to determining the weighted score based on the user analysis profiles output from the first machine learning model;
   generating a user analysis profile for the user by analyzing the received data using the first machine learning model, the user analysis profile comprising a personality profile for the user, a mood score related to a mood of the user, data reflecting interactions between others and the user, and symptom information relating to the user, the generating comprising:
      determining the personality profile using a portion of the received data relating to participation by the user in a social network;
      determining the mood score based on at least one of image recognition for an image in the received data or voice recognition for a voice in the received data;
      determining the data reflecting interactions between others and the user based on identifying interactions of others with the user in the received data; and
      determining the symptom information for the user based on data relating to user activity outside of social media;
   retrieving a previously determined weighted score associated with detecting a potential health issue for the user from an electronic database, wherein the previously determined weighted score is generated based on user analysis profile data;
   determining, by providing the user analysis profile to the second machine learning model, a second weighted score associated with detecting a potential health issue for the user, based on the determined personality profile for the user, the determined data reflecting interactions between others and the user, the determined symptom information relating to the user, the determined mood score for the user, and the retrieved previously determined weighted score, wherein the second machine learning model comprises continuous learning to learn from previous evaluations of the user;
   storing the determined second weighted score in the electronic database; and determining that the weighted score exceeds a pre-determined threshold, and in response providing an electronic notification to a pre-designated person regarding the potential health issue.

2. The method of claim 1, wherein the data reflecting interactions between others and the user comprises an instance of bullying of the user and the symptom information comprises an identified psychological symptom associated with the user, and wherein the weighted score is further based on analyzing the instance of bullying of the user and the identified psychological symptom.

3. The method of claim 1, further comprising sending an electronic instruction to an electronic social media source to modify content provided to the user.

4. The method of claim 1, wherein the received data further comprises real-time user data.

5. The method of claim 4, wherein the real-time user data comprises Global Positioning System (GPS) data and one or more of: key logger data and phone logger data.

6. The method of claim 4, further comprising:
ingesting the received data using an analytics engine that comprises a real-time analytics engine and a historical analytics engine, wherein the real-time analytics engine ingests the real-time user data, and wherein the historical analytics engine ingests the data related to social media activity for the user, wherein ingesting the data comprises modifying the data for use as input to the first machine learning model.

7. A system, comprising:
a processor; and
a memory storing a program, which, when executed on the processor, performs an operation, the operation comprising:
receiving data related to social media activity for a user, over a communications network, from one or more computing devices at a computing system comprising:
a first machine learning model trained to generate user analysis profiles using social media activity, wherein the first machine learning model is trained using a first plurality of feature vectors generated from training data comprising a first plurality of pre-determined attribute values relating to generating the user analysis profiles using social media activity; and
a second machine learning model trained to generate weighted scores associated with detecting potential health issues using the user analysis profiles output from the first machine learning model, wherein the first machine learning model is different than the second machine learning model, wherein the first machine learning model is trained using different training data than the second machine learning model, and wherein the second machine learning model is trained using a second plurality of feature vectors generated from training data comprising a second plurality of pre-determined attribute values relating to determining the weighted score based on the user analysis profiles output from the first machine learning model;
generating a user analysis profile for the user by analyzing the received data using the first machine learning model, the user analysis profile comprising a personality profile for the user, a mood score related to a mood of the user, data reflecting interactions between others and the user, and symptom information relating to the user, the generating comprising:
determining the personality profile using a portion of the received data relating to participation by the user in a social network;
determining the mood score based on at least one of image recognition for an image in the received data or voice recognition for a voice in the received data;
determining the data reflecting interactions between others and the user based on identifying interactions of others with the user in the received data; and
determining the symptom information for the user based on data relating to user activity outside of social media;
retrieving a previously determined weighted score associated with detecting a potential health issue for the user from an electronic database, wherein the previously determined weighted score is generated based on user analysis profile data;
determining, by providing the user analysis profile to the second machine learning model, a second weighted score associated with detecting a potential health issue for the user, based on the determined personality profile for the user, the determined data reflecting interactions between others and the user, the determined symptom information relating to the user, the determined mood score for the user, and the retrieved previously determined weighted score, wherein the second machine learning model comprises continuous learning to learn from previous evaluations of the user;
storing the determined second weighted score in the electronic database; and
determining that the weighted score exceeds a pre-determined threshold, and in response providing an electronic notification to a pre-designated person regarding the potential health issue.

8. The system of claim 7, wherein the data reflecting interactions between others and the user comprises an instance of bullying of the user and the symptom information comprises an identified psychological symptom associated with the user, and wherein the weighted score is further based on analyzing the instance of bullying of the user and the identified psychological symptom.

9. The system of claim 7, further comprising sending an electronic instruction to an electronic social media source to modify content provided to the user.

10. The system of claim 7, wherein the received data further comprises real-time user data, the operation further comprising:
ingesting the received data using an analytics engine that comprises a real-time analytics engine and a historical analytics engine, wherein the real-time analytics engine ingests the real-time user data, and wherein the historical analytics engine ingests the data related to social media activity for the user, and wherein ingesting the data comprises modifying the data for use as input to the first machine learning model.

11. A computer program product for detecting a possible health issue in a user, the computer program product comprising:
a computer-readable storage medium having computer-readable program code embodied therewith, the computer-readable program code executable by one or more computer processors to perform an operation, the operation comprising:

receiving data related to social media activity for a user, over a communications network, from one or more computing devices at a computing system comprising:
- a first machine learning model trained to generate user analysis profiles using social media activity, wherein the first machine learning model is trained using a first plurality of feature vectors generated from training data comprising a first plurality of pre-determined attribute values relating to generating the user analysis profiles using social media activity; and
- a second machine learning model trained to generate weighted scores associated with detecting potential health issues using the user analysis profiles output from the first machine learning model, wherein the first machine learning model is different than the second machine learning model, and wherein the first machine learning model is trained using different training data than the second machine learning model, and wherein the second machine learning model is trained using a second plurality of feature vectors generated from training data comprising a second plurality of pre-determined attribute values relating to determining the weighted score based on the user analysis profiles output from the first machine learning model;

generating a user analysis profile for the user by analyzing the received data using the first machine learning model, the user analysis profile comprising a personality profile for the user, a mood score related to a mood of the user, data reflecting interactions between others and the user, and symptom information relating to the user, the generating comprising:
- determining the personality profile using a portion of the received data relating to participation by the user in a social network;
- determining the mood score based on at least one of image recognition for an image in the received data or voice recognition for a voice in the received data;
- determining the data reflecting interactions between others and the user based on identifying interactions of others with the user in the received data; and
- determining the symptom information for the user based on data relating to user activity outside of social media;

retrieving a previously determined weighted score associated with detecting a potential health issue for the user from an electronic database, wherein the previously determined weighted score is generated based on user analysis profile data;

determining, by providing the user analysis profile to the second machine learning model, a second weighted score associated with detecting a potential health issue for the user, based on the determined personality profile for the user, the determined data reflecting interactions between others and the user, the determined symptom information relating to the user, the determined mood score for the user, and the retrieved previously determined weighted score, wherein the second machine learning model comprises continuous learning to learn from previous evaluations of the user;

storing the determined second weighted score in the electronic database; and determining that the weighted score exceeds a pre-determined threshold, and in response providing an electronic notification to a pre-designated person regarding the potential health issue.

12. The computer program product of claim 11, wherein the data reflecting interactions between others and the user comprises an instance of bullying of the user and the symptom information comprises an identified psychological symptom associated with the user, and wherein the weighted score is further based on analyzing the instance of bullying of the user and the identified psychological symptom.

13. The computer program product of claim 11, further comprising sending an electronic instruction to an electronic social media source to modify content provided to the user.

14. The computer program product of claim 11, wherein the received data further comprises real-time user data, the operation further comprising:
ingesting the received data using an analytics engine that comprises a real-time analytics engine and a historical analytics engine, wherein the real-time analytics engine ingests the real-time user data, and wherein the historical analytics engine ingests the data related to social media activity for the user, and wherein ingesting the data comprises modifying the data for use as input to the first machine learning model.

* * * * *